United States Patent [19]
Nixon et al.

[11] Patent Number: 5,449,671
[45] Date of Patent: * Sep. 12, 1995

[54] USE OF TGF-$\beta_3$, TO PREVENT OR RETARD FISTULA CLOSURE FOLLOWING GLAUCOMA FILTRATION SURGERY

[75] Inventors: Jon C. Nixon; Billie M. York, both of Fort Worth, Tex.

[73] Assignee: Alcon Labortories, Inc., Fort Worth, Tex.

[*] Notice: The portion of the term of this patent subsequent to May 2, 2012 has been disclaimed.

[21] Appl. No.: 129,962
[22] Filed: Sep. 29, 1993
[51] Int. Cl.$^6$ ............................................. A61K 38/00
[52] U.S. Cl. ....................................... 514/12; 514/21
[58] Field of Search .................................. 514/12, 21
[56] References Cited

U.S. PATENT DOCUMENTS

| | | | |
|---|---|---|---|
| 5,057,494 | 10/1991 | Sheffield | 514/12 |
| 5,108,989 | 4/1992 | Amento et al. | 514/12 |
| 5,124,392 | 6/1992 | Robertson | 514/427 |

FOREIGN PATENT DOCUMENTS

| | | | |
|---|---|---|---|
| 019018 | 8/1986 | European Pat. Off. | 37/2 |
| WO93/19769 | 10/1993 | WIPO | A61K 37/02 |
| WO94/01124 | 1/1994 | WIPO | A61K 37/02 |

OTHER PUBLICATIONS

Cheifelz et al, "Distinct Transforming Factor-$\beta$ . . . to Three TGF-$\beta$ Isoforms", J. Biological Chem., vol. 265 No. 33, pp. 20533 (1990).

Ferguson, W. F. "Wound Healing, Scarring and TGF-$\beta$ Isoforms", Abstract, Conference on TGF-$\beta$s: Biological and Clinical Applications, May 4–6, 1994, NIH, Bethesda, Md.

Tahery, M. M., et al., "Pharmacologic Control of Wound Healing in Glaucoma Filtration Surgery", Journal of Ocular Pharmacology, vol. 5, No. 2, pp. 155–179 (1989).

Tripathi, R. C., "Growth Factors in the Aqueous Humor and Their Therapeutic Implications in Glaucoma and Anterior Segment Disorders of the Human Eye", Drug Development Research, vol. 22, pp. 1–23 (1991).

Costa, V. P., et al, "Wound Healing Modulation in Glaucoma Filtration Surgery", Opthalmic Surgery, ; vol. 24, No. 3, pp. 152–170 (Mar. 1993).

Textbook of Glaucoma (2nd ed.), ed. M. Bruce Shields, M.D., "Glaucoma Filtering Procedures", Chapter 34, pp. 461–487, Baltimore, Md.: Williams & Wilkins (1987).

Derynck, R., et al., "A new type of transforming growth factor-$\beta$, TGF-$\beta_3$", EMBO Journal, vol. 7, NO. 12, pp. 3737–3743 (1988).

Connor Jr., T. B., et al., "Correlation of Fibrosis and Transforming Growth Factor-$\beta$ Type 2 Levels in the Eye", The American Society for Clinical Investigation, Inc., vol. 83, pp. 1661–1666 (May 1989).

ten Dijke, P., et al., "Identification of another member of the transforming growth factor type $\beta$ gene family", Proc. Natl. Acad. Sci. USA, vol. 85, pp. 4715–4719 (Jul. 1988).

Levine, et al., American Journal Pathol., vol. 143, pp. 368–380 (1993).

Smiddy, W., et al., "Transforming Growth Factor Beta", Archives of Ophthalmology, vol. 107, No. 1, pp. 577–580 (1989).

Glaser, B., et al., "Transforming Growth Factor-$\beta_2$ for the Treatment of Full-thickness Mascular Holes", Ophthalmology, vol. 99, No. 7, pp. 1162–1178 (1992).

Glaser, B., et al., "Induction of a 'Retinal Patch' By Transforming Growth Factor-Beta in the Treatment of Full Thickness Macular Holes", Investigative Ophthalmology & Visual Science, vol. 32, No. 4, p. 713 (Mar. 1991).

S. J. Ryan Chief Editor, "Retina", Chapter 68, published 1989 by the C. V. Mosby Company (St. Louis), pp. 229–242.

Primary Examiner—Jill Warden
Assistant Examiner—Plynn Touzeau
Attorney, Agent, or Firm—James A. Arno; Gregg C. Brown

[57] ABSTRACT

The intraocular use of TGF-$\beta_3$ in connection with glaucoma filtration surgery is described. A composition containing TGF-$\beta_3$ is applied to the surgical site to suppress the production and/or alter the composition of extracellular matrix synthesized by fibroblasts at the surgical site, and thereby reduce the formation of scar tissue and consequent impairment of the outflow of aqueous humor through a fistula created during the surgery.

4 Claims, No Drawings

USE OF TGF-β3, TO PREVENT OR RETARD FISTULA CLOSURE FOLLOWING GLAUCOMA FILTRATION SURGERY

BACKGROUND OF THE INVENTION

The present invention relates to the field of ophthalmology. More specifically, the invention relates to the field of glaucoma filtration surgery.

The underlying causes of glaucoma are not fury understood. However, it is known that a principal symptom of this disease is elevated intraocular pressure. Elevations of intraocular pressure can ultimately lead to impairment or loss of normal visual function as a result of damage to the optic nerve. It is also known that the elevated intraocular pressure is caused by an excess of fluid (i.e., aqueous humor) within the eye. The excess intraocular fluid is believed to result from blockage or impairment of the normal drainage of fluid from the eye via the trabecular meshwork.

The current drug therapies for treating glaucoma attempt to control intraocular pressure by means of increasing the drainage or "outflow" of aqueous humor from the eye or decreasing the production or "inflow" of aqueous humor in the ciliary processes of the eye. Unfortunately, the use of drug therapy alone is not sufficient to adequately control intraocular pressure in some patients, particularly if there is a severe blockage of the normal passages for the outflow of aqueous humor. Such patients may require surgical intervention to restore the normal outflow of aqueous humor and thereby normalize or at least control their intraocular pressure. The outflow of aqueous humor can be improved by means of various intraocular surgical procedures known to those skilled in the art, such as trabeculectomy, posterior lip sclerectomy, trephine and thermal sclerostomy. These surgical procedures are collectively referred to herein as "glaucoma filtration surgery".

The procedures utilized in glaucoma filtration surgery generally involve the creation of a fistula to promote the drainage of aqueous humor. Although various procedures have been utilized, the procedures will typically include the creation of an elevation of the conjunctiva at the surgical site. This elevation is commonly referred to as the "filtering bleb". The filtering blebs which are most often associated with good intraocular pressure control are avascular and either low and diffuse or elevated with numerous cystic spaces. Studies have suggested that aqueous fluid in the filtering bleb usually filters through the conjunctiva and mixes with the tear film, or is adsorbed by vascular or perivascular conjunctival tissue.

Although glaucoma filtration surgery is generally successful initially, it is ultimately plagued in many cases by the formation of scar tissue which blocks the fistula created during the surgery. The following articles may be referred to for further background information concerning this problem:

1) Tahery, M. M., et at., "Pharmacologic Control of Wound Healing in Glaucoma Filtration Surgery", *Journal of Ocular Pharmacology*, Vol. 5, No. 2, pages 155-179 (1989);

2) Tripathi, R. C., "Growth Factors in the Aqueous Humor and Their Therapeutic Implications in Glaucoma and Anterior Segment Disorders of the Human Eye", *Drug Development Research*, Vol. 22, pages 1-23 (1991); and 3) *Textbook of Glaucoma* (2nd ed.), ed. M. Bruce Shields, M.D., "Glaucoma Filtering Procedures", Chapter 34, pages 461-487, Baltimore Md.: Williams & Wilkins (1987).

The most common cause of failure in glaucoma filtration surgery is closure of the fistula as the result of scar tissue formation and other manifestations of the normal wound healing process. The increased amount of collagen in the failed fistulas suggests that proliferation of fibroblasts and associated production of extracellular matrix materials, particularly collagen, fibronectin and glycosaminoglycans, may lead to fistula failure.

As indicated in the above-cited article by Tahery, et at., the use of drugs to inhibit or control the wound healing process, and thereby limit the formation of scar tissue in glaucoma filtration surgery, has been previously proposed. The article mentions various types of drugs as potential inhibitors of the wound healing process, including anti-inflammatory drugs and anti-proliferative drugs. However, the use of such drugs to prevent scar formation associated with glaucoma filtration surgery has had very limited success. One reason for this lack of success is that the wound healing process does not take place instantaneously. Consequently, it is not possible to simply prevent scar formation by means of a single application of the drugs mentioned by Tahery, et al., at the time of surgery. Moreover, many of those drugs, when utilized to prevent scar formation, are inherently toxic to ophthalmic tissues other than the tissues directly involved in the surgically induced wound healing process, particularly at higher concentrations. This potential toxicity precludes the use of high drag concentrations which might otherwise be considered desirable in order to control or at least suppress the formation of extracellular matrix materials and scar tissue associated with wound closure following glaucoma filtration surgery. Moreover, even with the use of antiproliferative agents such as 5'-fluorouracil, the failure rate (i.e., total blockage of fistula) in high-risk groups, such as patients with previous failed filtering surgery, previous cataract extraction, aphakia, or neovascular glaucoma, is still significant. In addition, many of the antiproliferative drugs used may be associated with complications such as corneal or conjunctival epithelial loss, corneal opacification, and wound leaks, and the possibility of long-term leaks and endophthalmitis related to extremely thin blebs which can occur with drug treatment. The use of single-dose, intra-operative exposures to antiproliferative agents such as mitomycin C may reduce some of these problems, but the problems with thin blebs and hypotony will still exist.

In view of the foregoing circumstances, there is a need for an improved drug therapy to complement glaucoma filtration surgery, so that the improved outflow of aqueous humor achieved by means of the surgery is not ultimately lost as the result of closure of the surgical fistula by scar tissue. The present invention is directed to satisfying this need.

SUMMARY OF THE INVENTION

The present invention provides a method to prevent or retard the formation of scar tissue in connection with glaucoma filtration surgery, and thereby reduce the incidence of fistula closure. The method of the present invention utilizes a specific growth factor, transforming growth factor-beta-3 ("TGF-$\beta_3$"), as a mediator of the normal wound healing process.

Three mammalian ("TGF-$\beta$") isoforms of transforming growth factor-beta ("TGF-$\beta$"), denoted as $\beta_1$, $\beta_2$, and $\beta_3$, respectively, have been identified. Each has a different specific gene loci. While the primary amino acid structure of these isoforms is highly conserved, there are clear differences in both the mature bioactive region and in the latency-associated peptide, both of which may confer biological specificity. See Akhurst, et at., *Mol. Reproduc. Dev.*, volume 32, pages 127–135 (1992). These isoforms have been found to share many of their biological activities at the cellular level. See Graycar, et al., *Mol. Endocrinol.*, volume 3, pages 1977–1986 (1989). However, it is being discovered that the isoforms may have quite different in vivo functions.

In studies on fetal wounds, it has been noted that healing occurs rapidly without the scarring associated with the healing of adult wounds. Fetal wounds are thought to have relatively high levels of TGF-$\beta_3$. TGF-$\beta_1$ and basic fibroblast growth factor are present in neonatal and adult wounds, but are not detected in fetal wounds. See Whitby, et at., *Devl. Biol.*, volume 147, pages 207–215 (1991). If fetal wounds are injected with TGF-$\beta_1$, scarring will occur, and if a specific antibody to TGF-$\beta_1$ is added to the wound, neutralizing the effects of the growth factor, scarfing will be prevented. See Shah, et at., *Lancet*, volume 339, pages 213–214 (1992).

TGF-$\beta_1$ regulates extracellular matrix synthesis by a variety of mechanisms. See Amento, et al., *Ciba Foundation Symposium*, volume 157, pages 115–129 (1991). It stimulates the synthesis and secretion of extracellular matrix proteins, including collagen and fibronectin. In addition, it increases the expression of integrins and other membrane receptors which may facilitate cell migration into the wound. TGF-$\beta_1$ has also been shown to decrease the synthesis of proteases that degrade extracellular matrix, and stimulates the synthesis of endogenous protease inhibitors. All of these responses have been measured in fibroblasts; however, it is important to note that all fibroblasts do not respond in the same way to TGF-$\beta_1$. For example, collagen synthesis in fibroblasts isolated from the colon is suppressed by TGF-$\beta_1$. See Martens, et at., *Gut*, volume 33, pages 1664–1670 (1992).

In normal wound repair in an adult, marked differences are noted in the temporal and spacial relationships of the $\beta_1$, $\beta_2$, and $\beta_3$ isoforms of TGF-$\beta$ throughout the repair process. TGF-$\beta_2$ and TGF-$\beta_3$ are prevalent at 24 hours after excisional wounding and are associated with the migrating epidermis. In contrast, TGF-$\beta_1$ is not associated with any undifferentiated cells and is not present in the dermis and most dermal structures until five days after wounding, when re-epithelialization is completed. Following re-epithelialization, TGF-$\beta_2$ and TGF-$\beta_3$ are present in all four layers of the stratum corneum of the differentiating epidermis. This strongly suggests a role for TGF-$\beta_3$ in dermal-epidermal interactions during wound repair. See Levine, et at., *Am. J. Pathol.*, volume 143, pages 368–380 (1993).

In view of the foregoing, it is clear that there are distinct differences between the in vivo activities of the $\beta_1$, $\beta_2$, and $\beta_3$ isoforms of TGF-$\beta$. This is particularly true with respect to TGF-$\beta_3$. The present invention is based on a new application of the unique properties of TGF-$\beta_3$. More specifically, the present invention utilizes the properties of TGF-$\beta_3$ to alter the healing of wounds associated with glaucoma filtration surgery, so as to reduce the incidence of fistula closure by scar tissue.

While applicants do not wish to be bound by any theory, it is believed that TGF-$\oplus_3$ prevents or retards the formation of scar tissue at the surgical site, particularly the surgical fistula, by suppressing the secretion of certain extracellular matrix components by fibroblasts. The suppression and alteration of the composition of the extracellular matrix, particularly fibronectin, collagen and glycosaminoglycans, greatly reduces the formation of scar tissue at the site of the glaucoma filtration surgery. The reduction of scar tissue formation enables the fluid passageway formed by the surgery to remain open and intact.

The above-described method provides a significant improvement in the ability to prevent or retard the formation of scar tissue which might otherwise lead to closure of surgical fistulas created during glaucoma filtration surgeries.

DESCRIPTION OF PREFERRED EMBODIMENTS

TGF-$\beta_3$ is one of five known forms of transforming growth factor-beta ("TGF-$\beta$"). The composition and properties of this polypeptide have been previously described in scientific and patent literature. See, for example, U.S. Pat. No. 5,108,989 (Amento, et al.; Genentech, Inc.), and the publications cited therein, particularly the following two scientific articles:

1) Derynck, et al., *EMBO J.*, Vol. 7, pages 3737–3743 (1988); and 2) ten Dijke, et at., *Proc. Natl. Acad. Sci. USA*, vol. 85, page 4715 (1988).

The entire contents of the above-cited publications relating to the properties of TGF-$\beta_3$ and procedures for isolating this polypeptide are hereby incorporated in the present specification by reference. The TGF-$\beta_3$ utilized in the present invention is preferably human derived. As used herein, the term "human derived" encompasses TGF-$\beta_3$ recovered from human tissues and TGF-$\beta_3$ produced from human cell lines by means of recombinant DNA technology.

The compositions utilized in the present invention contain TGF-$\beta_3$ in an amount sufficient to suppress the formation and alter the composition of extracellular matrix synthesized by fibroblasts at the site of the glaucoma filtration surgery. The amount of TGF-$\beta_3$ required for this purpose will generally be from about 0.01 nanograms per milliliter ("ng/ml") to about 100 micrograms per milliliter ("$\mu$g/ml"). The preferred range is from about 1 to about 500 ng/ml.

TGF-$\beta_3$ can be included in various types of pharmaceutical vehicles suitable for intraocular use. The vehicles are preferably aqueous, and are formulated so as to be chemically and physically compatible with ophthalmic tissues. For example, TGF-$\beta_3$ may be included in aqueous irrigating solutions, bioerodible gels or collagen inserts. The use of such gels or inserts has the advantage of providing sustained release of TGF-$\beta_3$ at the surgical site. However, the use of an aqueous solution as the vehicle for TGF-$\beta_3$ may be preferred in some cases due to the potential for blockage of the filtering bleb by erodible gels or other solid or semi-solid inserts. The aqueous solutions which might be utilized must be compatible with intraocular tissues, and should preferably help to maintain the integrity and function of intraocular tissues during the surgical procedure. The aqueous solutions which might be utilized for the above-described purposes include balanced saline solutions, such as BSS ® Balanced Salt Solution and BSS Plus ® Balanced Salt Solution Enriched with Bicarbonate, Dextrose and Glutathione, both of which are available from Alcon Surgical, Inc., Fort Worth, Tex.

As will be appreciated by those skilled in the art, the above-described compositions must be sterile and should not include any agents (e.g., antimicrobial preservatives) which will be toxic to sensitive intraocular tissues, particularly corneal endothelial cells. The above-described compositions can be formulated in accordance with techniques known to those skilled in the art.

The above-described compositions can be applied to the surgical site by means of various techniques. For example, the compositions can be applied by means of a syringe during or immediately after surgery. The only critical requirement with respect to how the compositions are applied is that the compositions be distributed throughout the surgical site, particularly the fistula, and remain in contact with the surgical site for a length of time sufficient to alter the formation of extracellular matrix components by fibroblasts at the surgical site, thereby preventing or retarding the formation of scar tissue. The amount of time required to achieve this purpose will vary somewhat depending on circumstances such as the particular type of glaucoma filtration surgery being performed. However, the compositions will generally need to remain in contact with the surgical site for at least five to ten minutes, or longer. The compositions can be removed by means of irrigation and aspiration. However, in some cases, it may be desirable to leave the composition in place and allow the composition to be gradually washed out of the wound site by the aqueous humor.

What is claimed is:

1. A method of reducing the formation of scar tissue following glaucoma filtration surgery, which comprises applying to the surgical site at the time of surgery a composition comprising: 0.01.ng/ml to 100 µg/ml of TGF-$\beta_3$ and a pharmaceutically acceptable vehicle therefor.

2. A method according to claim 1, wherein the composition comprises TGF-$\beta_3$ in an amount of 1 ng/ml to 500 ng/ml.

3. A method according to claim 1, wherein the composition is applied to a fistula created during the glaucoma filtration surgery.

4. A method according to claim 1, wherein the TGF-$\beta_3$ is human derived.

* * * * *